US 6,957,909 B1

(12) United States Patent  
Dingeldein et al.

(10) Patent No.: US 6,957,909 B1  
(45) Date of Patent: Oct. 25, 2005

(54) BLISTER PACK

(75) Inventors: Elvira Dingeldein, Dreieich (DE); Helmut Wahlig, Darmstadt (DE); Christoph Sattig, Dieburg (DE); Edgar Wüst, Rodgau (DE)

(73) Assignee: Smith & Nephew, Inc., Memphis, TN (US)

( * ) Notice: Subject to any disclaimer, the term of this patent is extended or adjusted under 35 U.S.C. 154(b) by 901 days.

(21) Appl. No.: 09/980,547

(22) PCT Filed: Jul. 20, 2000

(86) PCT No.: PCT/EP00/06920

§ 371 (c)(1),  
(2), (4) Date: Oct. 19, 2001

(87) PCT Pub. No.: WO01/07337

PCT Pub. Date: Feb. 1, 2001

(30) Foreign Application Priority Data

Jul. 24, 1999 (DE) .................... 299 12 954 U

(51) Int. Cl.⁷ .................... B65D 71/00; B65D 69/00; B01F 15/00
(52) U.S. Cl. .................... 366/130; 366/189; 220/221; 220/222; 220/557; 220/568
(58) Field of Search .................... 206/568, 219, 206/223, 528, 538, 540, 524.1–524.7, 822, 206/828, 460, 471, 220, 563, 467, 469; 220/528, 220/555, DIG. 13, 525, 526, 523, 557, 359.2, 220/359.1, 359.3, 831; 215/DIG. 8; 366/130, 366/189

(56) References Cited

U.S. PATENT DOCUMENTS

| | | | | |
|---|---|---|---|---|
| 3,618,751 A | * | 11/1971 | Rich | 206/219 |
| 4,008,803 A | * | 2/1977 | Smith | 206/220 |
| 4,294,349 A | * | 10/1981 | Ibsen et al. | 206/568 |
| 4,697,703 A | * | 10/1987 | Will | 206/828 |
| 4,844,251 A | * | 7/1989 | Gueret | 206/823 |
| 5,240,415 A | * | 8/1993 | Haynie | 206/63.5 |
| 5,975,305 A | * | 11/1999 | Barger | 206/572 |
| 6,364,519 B1 | * | 4/2002 | Hughes et al. | 206/568 |

* cited by examiner

Primary Examiner—Tony G Soohoo

(57) ABSTRACT

Blister packaging unit (10) for at least two components packed in separate individual packages, at least one of which has a pulverulent or granular consistency, which are to be prepared before use with the further packaged component(s) in a mixer or applicator to form a ready-to-use mixture. The individual packages of the components are inserted in correspondingly pre-shaped receptacles (32; 34) in the blister (30) of a suitable film or other material and this blister is closed on the side of the open mouth of the receptacles by a cover (36) of cardboard, plastic, metal or some other suitable material which may be torn off or opened in some other manner.

The component(s) having the pulverulent or granular consistency is/are packaged in a respective individual blister pack (12; 14; 16) shaped at least approximately complementarily to the associated receptacle (32) in the blister packaging unit, the blister of which has the shape of an elongate trough element (12) of plastic material tapered at at least one end in the manner of a spout, which trough element(s) comprises a separate tear-off cover (16) of cardboard, plastic, metal or some other suitable material which may be torn off or opened in some other manner.

22 Claims, 3 Drawing Sheets

BLISTER PACK

BACKGROUND OF THE INVENTION

The invention relates to a blister packaging unit in which at least two different components are retained captive, at least one of which has a pulverulent or granular consistency and which are to be treated before use with the further packaged component(s) in a mixer or applicator to form a ready-to-use mixture, the components being inserted in appropriately preformed receptacles in the blister of a suitable film or other material and the latter is closed on the side of the open mouth of the receptacles by a cover of cardboard, plastic, metal or some other suitable material which may be torn off or opened in some other way.

Blister packages, in which the packed product is inserted in preformed receptacles in a blister of a stiff plastic film and is held secured against loss by a cover of cardboard, film or the like glued, sealed or clipped to the open mouth side of the blister are known. If the material inserted into the receptacles of the blister package has a predetermined external shape, the receptacles in the blister are shaped complementarily to the outline of the material to be accommodated, for instance somewhat oversized, in order to maintain its predetermined position in the blister package stable and—in the case of shock—or pressure-sensitive material—to protect it against damage in the event of careless handling. It is also possible to arrange components which are different but are required together in later use in a plurality of matched receptacles in a blister and to protect them from loss until they are used by means of a common cover.

A blister packaging unit of the type referred to above is disclosed in U.S. Pat. No. 4,844,251 in which one of the components, which are contained in associated receptacles in the blister, has a pulverulent or granular consistency.

SUMMARY OF THE INVENTION

It is the object of the invention to improve the known blister packaging unit so that the components can be introduced into a mixer or applicator without loss and prepared to form a ready-to-use mixture.

Starting from a blister packaging unit of the type referred to above, this object is solved in accordance with the invention if the different components are packed separated from one another in separate individual packages, of which the component(s) having the pulverulent or granular consistency is/are packaged in an individual blister package which is shaped at least approximately complementarily to the associated receptacle in the blister, the blister of which has the shape of an elongate trough element of plastic tapered in the manner of a spout at at least one end, whereby the trough element(s) is closed by a separate tear-off cover of cardboard, plastic, metal or some other suitable material which may be torn off or opened in some other manner. The pulverulent or granular component can, for instance, be a predetermined amount of a polymer, which can be prepared before use with a predetermined amount of a liquid monomer, conveniently stored in a glass container in a second receptacle in the blister to form a hardening or setting adhesive or cement. The construction of the blister accommodating the pulverulent or granular component in the form of a trough element with an end tapered in the manner of a spout ensures that this component can be introduced without loss into the mixer or applicator so that the predetermined mixing ratio of the finished product is ensured.

The blister packaging unit in accordance with the invention is appropriate for the metered packaging of the components of a bone cement to be used in human medicine, particularly surgical orthopaedics, whereby the pulverulent or granular polymer is prepared in an applicator directly before use to form a pasty composition for processing. The component(s) having the pulverulent or granular consistency, i.e. the polymer, is then packaged in a sterile manner in the associated blister pack. With an appropriate selection of the material of the cover of the blister pack for the polymer, this sterilisation can also be effected subsequently by appropriate gas treatment or alternatively by radiation sterilisation. Alternatively, the sterile introduction of the liquid component (monomer) into a glass tube etc. represents no technical problem.

BRIEF DESCRIPTION OF THE DRAWINGS

The invention will be explained in more detail in the following description of one exemplary embodiment in conjunction with the drawings, in which.

DETAILED DESCRIPTION OF THE PREFERRED EMBODIMENTS

Figure 1:
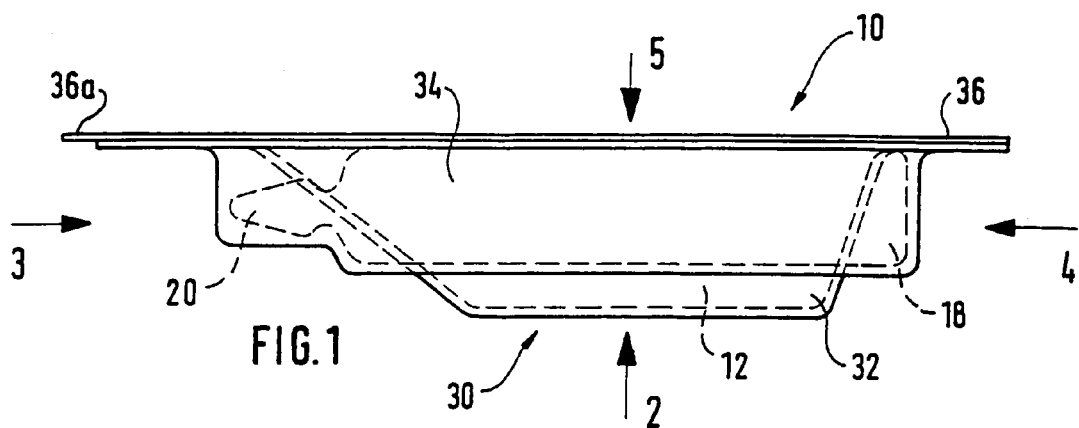
FIG. 1 is a side view of an exemplary embodiment of a blister packaging unit in accordance with the invention, which is intended for the sterile and metered storage and provision of two components intended for mixing before use in a suitable mixer and/or applicator, one of which in the special case has a pulverulent or granular consistency and the other has a liquid consistency.
Figure 2:
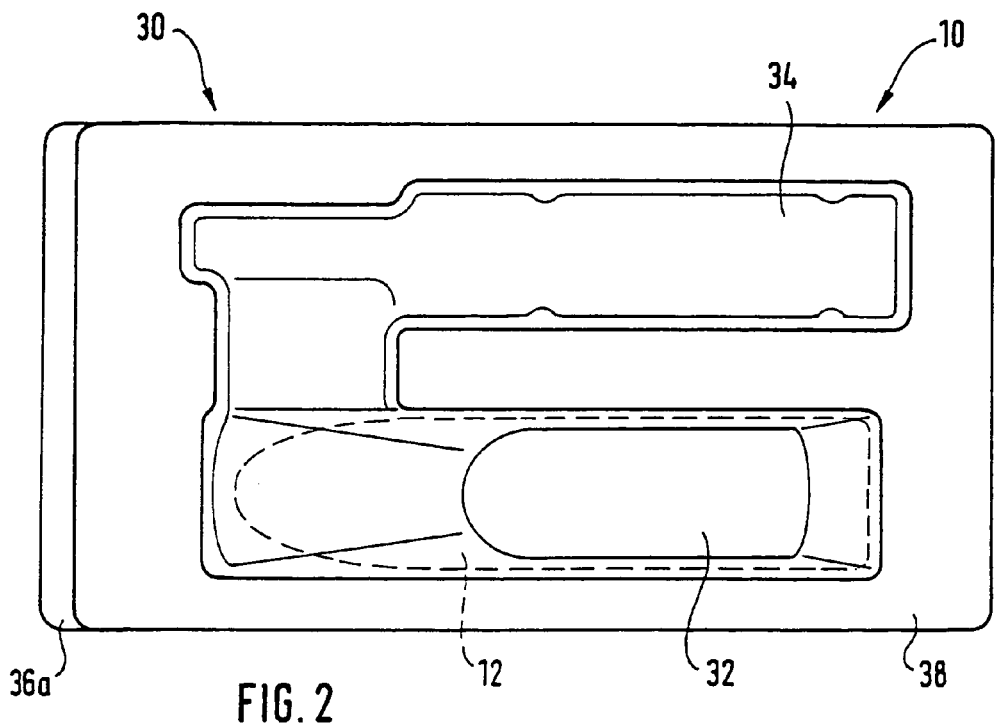
FIG. 2 is an underneath view of the blister packaging unit, seen in the direction of the arrow 2 in FIG. 1.
Figures 3, 4:
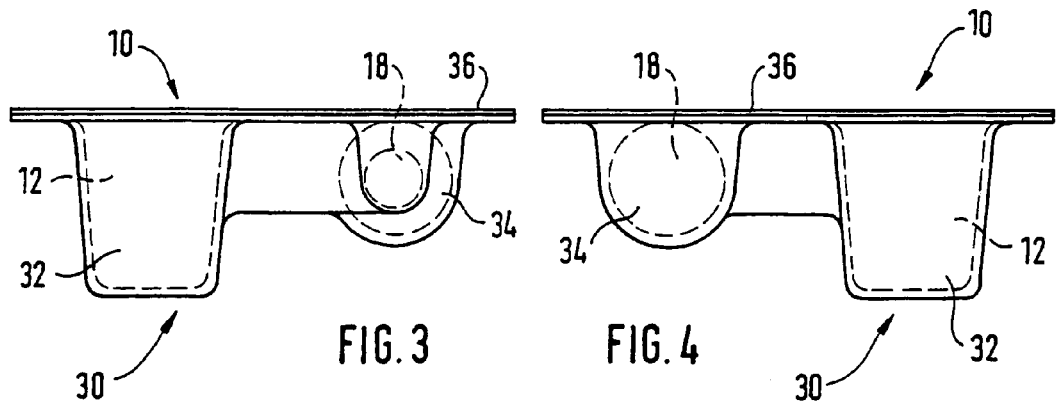
FIG. 3 is a view of the blister packaging unit, seen in the direction of the arrow 3 in FIG. 1.
FIG. 4 is a view of the blister packaging unit, seen in the direction of the arrow 4 in FIG. 1.

The exemplary embodiment illustrated in the drawings represents a blister packaging unit, designated 10 as a whole, for the components of a two-phase bone cement, which is to be prepared directly before use by mixing and comprises a pulverulent solid phase of polymethylmethacrylate and a liquid phase of monomeric methylmethacrylate, whereby further substances can be added to the pulverulent solid phase as a catalyst and additional liquid components constituting accelerators and stabilisers or further additives can be added to the liquid phase. The two components are mixed directly before use to form a plastic product which sets in the course of time and is used e.g. in orthopaedic surgery to fix prostheses.

The pulverulent or granular polymer component—together with any additives—is introduced in the provided amount into a blister, which is constructed in the form of an elongate trough element 12, which is hermetically sealed by a cover of cardboard, paper, film or a paper-film laminate secured by adhesive to a flat peripheral flange 14 formed on its free edge. The necessary sterility of the polymer components is ensured by suitable techniques, e.g. gasification of the trough element, which is still open or is closed with a gas permeable material, with ethylene oxide or by the action of ionising radiation in a sufficient dose with the cover optionally already closed.

Figure 6:
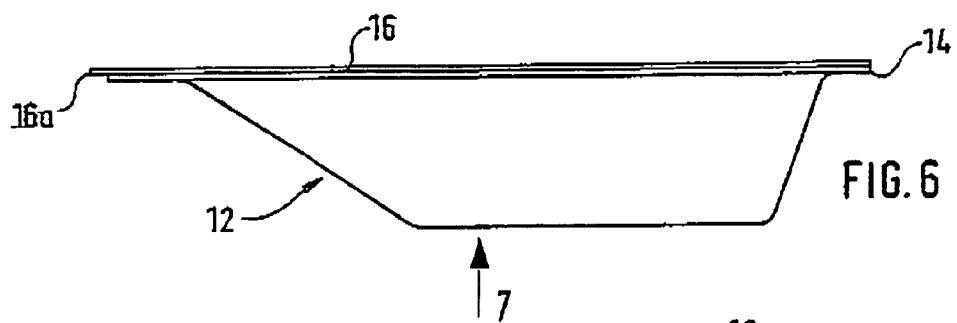
FIG. 6 is a side view of the separated blister package accommodating the pulverulent or granular components.
Figure 7:
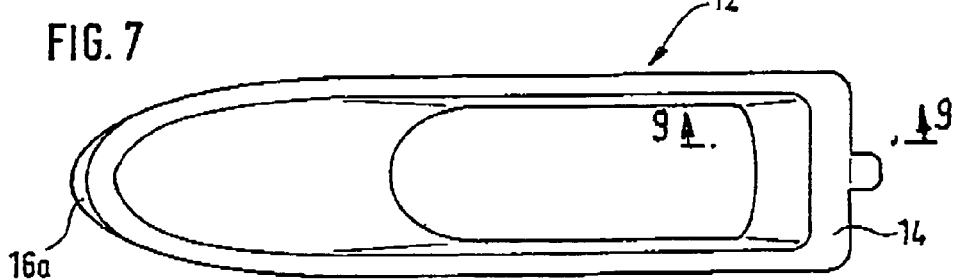
FIG. 7 is a view seen in the direction of the arrow 7 in FIG. 6.
Figure 8:
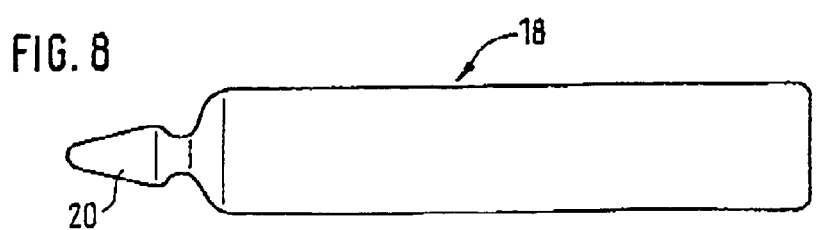
FIG. 8 is a side view of a glass tube accommodating the second component in the blister package of FIGS. 1 to 5.
Figure 9:
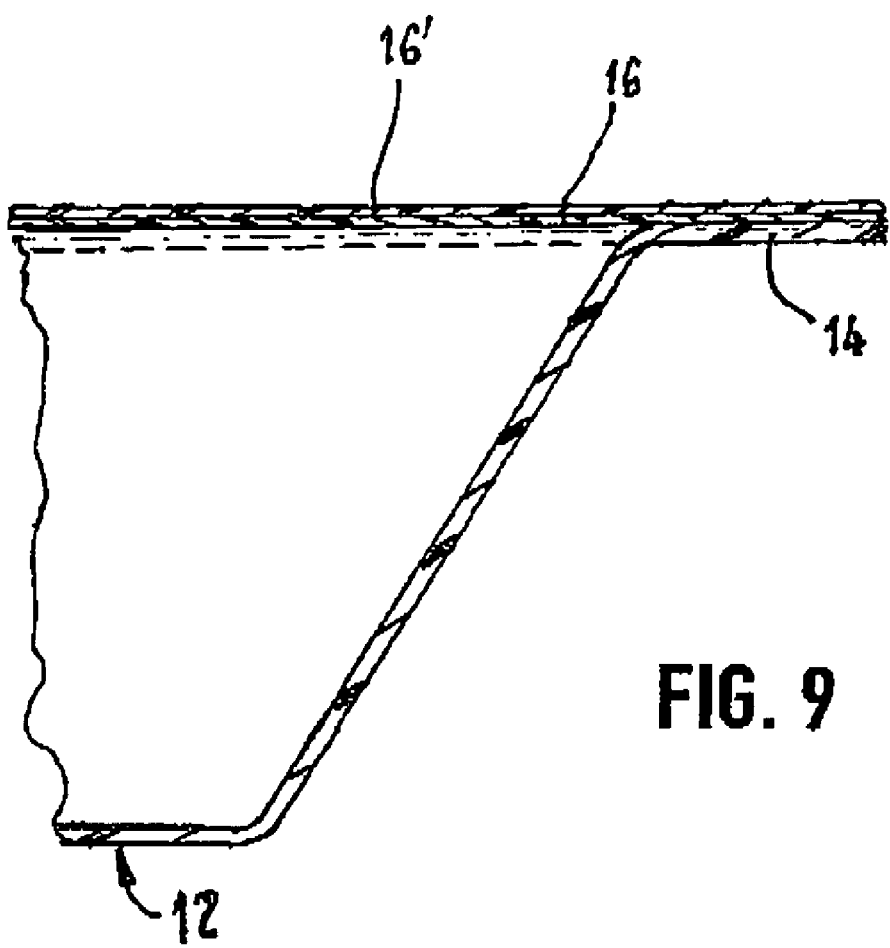
FIG. 9 is a cross-sectional view of an embodiment having two separate covers, taken through the line 9—9 of FIG. 7.

It may be seen in FIGS. 6 and 7 that the trough element 12 tapers at its left-hand end in the drawing in the manner of a spout and ascends obliquely upwards from the base so that the packaged component can be introduced without difficulty and without spillage, even into a narrow in-feed of a mixing and applicator device after tearing off the cover 16. In order to facilitate the opening process, i.e. the tearing off of the cover 16 from the trough element 12, the cover is enlarged in the front tapered spout region so that it constitutes a tear-off lug 16*a*.

A small cut in the latter makes it possible, when the trough element is only half open, to fold the cover towards the rear end and hang it on the enlarged portion in the rear end of the peripheral flange 14 of the trough element (FIG. 7). This facilitates the emptying of the contents and also prevents undesired dust formation when shaking out fine powder.

The second liquid or monomer component is introduced in a sterile manner in the amount achieving the optimal desired properties for the mixing into an elongate cylindrical glass tube 18 with an integrally attached outlet nozzle 20, which may be broken off and is hermetically sealed after being filled with the monomer by melting its open aperture.

Figure 5:
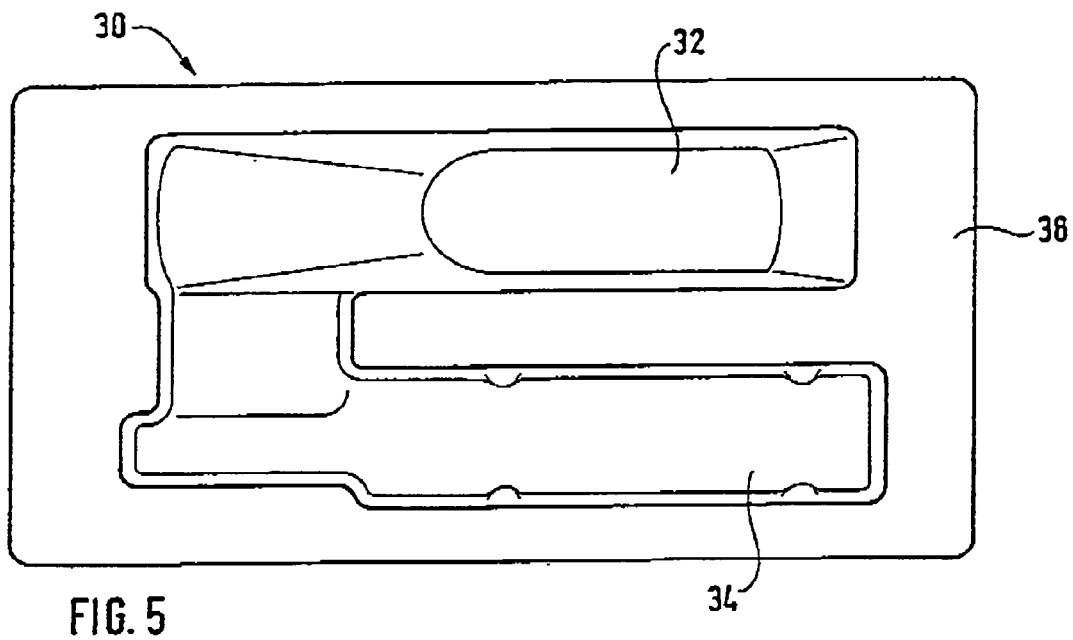
FIG. 5 is a plan view of the blister packaging unit with the cover removed and without the inserted individual packages for the two components, seen in the direction of the arrow 5 in FIG. 1.

The packaging of the two components, which are captive until use and secured against damage, is effected in the aforementioned blister packaging unit 10, which is shown in FIGS. 1 to 4 and consists of the actual blister 30 (FIG. 5) of plastic film, in which receptacles 32, 34 are formed corresponding approximately to the individual packages of the components, and a cover 36 of cardboard, paper, film or a paper-film laminate, which is glued or sealed to the flat edge flange 38 formed on the side of the open mouth of the receptacles 32, 34. The cover 36 can, at least on one boundary side, project somewhat beyond the edge flange 36 in the manner illustrated at the left-hand edge in FIG. 2 and then constitutes there a tear-off lug 36*a*.

The blister packaging unit 10 is so constructed that the peripheral flange can be closed successively with two different materials. Thus it is possible, in a first step after closure with a gas-permeable lid, to conduct, for instance, an ethylene oxide treatment for the purpose of sterilising the blister contents. In a second step, a hermetic sealing process can be effected by applying an air- and water vapour-tight cover, for instance of an aluminium laminated film.

It will be apparent that modifications and developments of the described exemplary embodiment may be realised within the scope of the inventive concept, which relate, for instance, to the number of components to be stored packed in separate individual packages in the blister packaging unit in accordance with the invention. Thus it is, for instance, possible to store two (or more) pulverulent or granular components in respective, separate packages, similar to the blister package 12, 14, 16, in the same blister packaging unit 10, which must then have an additional receptacle in the blister 30. Such a blister packaging unit is, for instance, convenient if, in the context of the application of the exemplary embodiment described above, the product to be prepared is additionally to contain a further, for instance pharmaceutically active, component, such as an antibiotic etc., which must be substantially homogeneously distributed in the mixture. If the additional component has a liquid consistency, it will in general be premixable with the liquid polymer. In powder or crystalline form, it can, however, be convenient firstly to mix this pharmaceutically active component in a high dosage with a proportion of the component having a pulverulent or granular consistency, i.e. the polymer component, and to adjust the proportion containing the finished mixture by the addition of the pulverulent or granular component without the pharmaceutically active substance, which is stored separately. Long-term incompatible liquid components can initially be stored in separate individual packages in associated receptacles in the blister package in accordance with the invention and are then only mixed together directly before use.

What is claimed is:

1. A blister packaging unit (10) in which at least two different components are retained captive, at least one of which has a pulverulent or granular consistency and is to be prepared before use with the further packaged component(s) in a mixer or applicator to form a ready-for-use mixture, whereby the components are inserted in appropriately pre-shaped receptacles (32; 34) in a packing unit blister (30) of a suitable film material, the blister being closed on a side of an open mouth of the receptacle by a cover (36) which may be opened to allow access to the component(s), wherein the different components are packed separated from one another in separate individual packages, of which the component(s) having the pulverulent or granular consistency is/are packaged in an individual blister package (12; 14; 16) which is shaped generally complementarily to an associated receptacle (32) in the packing unit blister, a blister of the individual blister package having a shape of an elongate trough element (12) of plastic tapered in the manner of a spout at at least one end, whereby the trough element(s) is closed by a separate tear-off cover (16) which may be opened to allow access to the component(s).

2. The blister packaging unit as claimed in Claim 1, in which the components having a pulverulent or granular consistency is/are packaged in a sterile manner and the sterility must be guaranteed until preparation to form the ready-to-use mixture wherein both the material of the trough element (12) and the material of the separate cover (16) and their connection is constructed to be impermeable to the passage of germs.

3. The blister packaging unit as claimed in claim 2, wherein the material of the trough element (12) and/or the separate cover (16) is constructed to be permeable to radiation with ionising beams for the purpose of radiation sterilisation of the component(s) having a pulverulent or granular consistency.

4. The blister packaging unit as claimed in claim 1, wherein the separate tear-off cover (16) is constructed to be permeable for gas treatment, for the purpose of sterilising the component(s) having a pulverulent or granular consistency.

5. Blister packaging unit as claimed in claim 1, wherein two separate covers (16) with different chemical, physical properties are applied in two successive steps to the peripheral flange (14) of the trough element (12).

6. A system for storing cement components comprising a container storing cement powder, and a lid, at least a portion of which is attached to the container and is capable of being peeled off the container to access the powder in the container, wherein the container has a bottom and at least one wall connected to the bottom, at least a portion of said wall slanting upwardly from the bottom.

7. The system of claim 6, wherein the container comprises plastic.

8. The system of claim 6, wherein the at least a portion of the lid is attached to the container with adhesive.

9. The system of claim 6, wherein the container further comprises a rim extending outwardly from the at least one wall.

10. The system of claim 9, wherein the at least a portion of the lid is attached to the rim of the container.

11. The system of claim 6, wherein the container further comprises a tab extending outwardly from the at least one wall.

12. The system of claim 6, wherein the at least one wall comprises a front wall, a back wall, and two side walls, wherein the front wall slants upwardly from the bottom and at least a portion of at least one of the side walls tapers towards the other side wall proximate to the front wall.

13. The system of claim 6, further comprising an ampoule containing a liquid monomer.

14. The system of claim 13, wherein the ampoule comprises glass.

15. The system of claim 6, wherein the container is adapted to mate with a funnel.

16. A method for storing cement components comprising:
a) inserting cement powder into a container comprising a closed bottom and at least one wall connected to the bottom, at least a portion of said wall slanting upwardly from the bottom; and
b) attaching a lid to at least a portion of the container to seal the powder into the container.

17. A method for making cement comprising:
a) providing a container storing cement powder and having a lid, at least a portion of said lid being attached to the container and capable of being peeled off the container to access the powder in the container, wherein the container has a closed bottom and at least one wall connected to the bottom, at least a portion of said wall slanting upwardly from the bottom;
b) peeling the lid at least partially from the container;
c) pouring the cement powder into a mixing bowl;
d) mixing a liquid monomer with the cement powder in the mixing bowl.

18. The method of claim 17, wherein the pouring of the cement powder into the mixing bowl further comprises guiding the powder from the container and into the mixing bowl using a funnel.

19. A system for mixing cement comprising:
a) a cement mixer having a mixing chamber with an opening;
b) a funnel member having an input end and an output end, wherein the output end mates with the opening of the mixer; and
c) a container storing cement powder, and a lid, at least a portion of which is attached to the container and is capable of being peeled off the container to access the powder in the container, wherein the container is adapted to mate with the input end of the funnel member.

20. The system of claim 19, wherein the container further comprises a tapered end to mate with the input end of the funnel member.

21. The system of claim 20, wherein the container further comprises a bottom, a front wall and two side walls, wherein the front wall slants upwardly from the bottom and at least a portion of at least one of the side walls tapers towards the other side wall proximate to the front wall to form the tapered end.

22. The system of claim 19, further comprising an ampoule containing a liquid monomer.

* * * * *